United States Patent [19]

Broger et al.

[11] Patent Number: 5,516,944
[45] Date of Patent: May 14, 1996

[54] OPTICALLY ACTIVE PHOSPHOROUS COMPOUNDS

[75] Inventors: Emil A. Broger, Magden; Marco Cereghetti, Basel, both of Switzerland; Alain Rageot, St. Louis, France

[73] Assignee: Hoffmann-La Roche Inc., Nutley, N.J.

[21] Appl. No.: 315,791

[22] Filed: Sep. 30, 1994

[30] Foreign Application Priority Data

Oct. 8, 1993 [CH] Switzerland .............................. 3038/93

[51] Int. Cl.⁶ ..................................................... C07F 9/02
[52] U.S. Cl. .................................. 568/13; 568/12; 568/17
[58] Field of Search ................................... 568/12, 13, 17

[56] References Cited

U.S. PATENT DOCUMENTS

| | | | |
|---|---|---|---|
| 4,556,740 | 12/1985 | Hansen et al. | 568/13 |
| 4,851,581 | 7/1989 | Devon et al. | 568/17 |
| 5,012,002 | 4/1991 | Kumobayashi et al. | 568/17 |
| 5,087,728 | 2/1992 | Nohira et al. | 566/41 |
| 5,274,125 | 12/1993 | Broger et al. | 549/216 |
| 5,302,738 | 4/1994 | Foricher et al. | 568/13 |
| 5,312,939 | 5/1994 | Hori et al. | 568/17 |

OTHER PUBLICATIONS

Noyori, et al., Chemica Scripta, vol. 25, pp. 83–89 (1985).
Nagel, et al., Chem. Ber. vol. 125, pp. 1061–1072 (1992).
Nagel, et al., Angew. Chem, Int. Ed. England, vol. 32, No. 7, (1993).
Juge, et al, Tetrahedron Letters, vol. 31, No. 44, pp. 6357–6360 (1990).
Nagel, et al, Angew. Chem. vol. 105, No. 7, pp. 1099–1101 (1993).
Nagel, et al, Chem. Ber. vol. 126, pp. 1091–1100 (1993).

*Primary Examiner*—James H. Reamer
*Attorney, Agent, or Firm*—George M. Gould; William H. Epstein; Bruce A. Pokras

[57] ABSTRACT

The present invention is concerned with novel optically active phosphorus compounds of the general formula

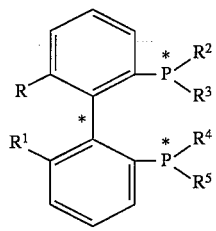

I wherein
R and R¹ each independently signify hydroxy, a protected hydroxy group, lower alkyl or lower alkoxy and
R² to R⁵ each independently signify alkyl with 3 to 7 carbon atoms, cycloalkyl or aryl or R² and R³ or R⁴ and R⁵ together with the phosphorus form a group of the formula

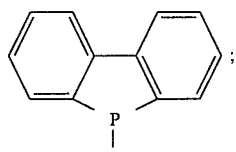

wherein R2 and R3 are different when R4 and R5 are the same, and R4 and R5 are different when R2 and R3 are the same,
the manufacture of such compounds, their use for enantioselective reactions, such as, e.g., asymmetric hydrogenations, enantioselective hydrogen displacements in prochiral allylic systems and the like, as well as complexes of the compounds of formula I with Group VIII metals.

31 Claims, No Drawings

OPTICALLY ACTIVE PHOSPHOROUS COMPOUNDS

SUMMARY OF THE INVENTION

The present invention is concerned with novel optically active phosphorus compounds, which, in addition to the pre-determined axial chirality of the biphenyl skeleton, also have centres of chirality at one or both phosphorus atoms, of the formula:

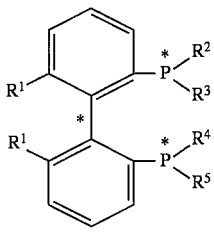     I wherein
$R^1$ is hydroxy, a protected hydroxy group, lower alkyl or lower alkoxy and
$R^2$ to $R^5$ each independently are alkyl with 3 to 7 carbon atoms, cycloalkyl or aryl, or $R^2$ and $R^3$ or $R^4$ and $R^5$ together with the phosphorus to which they are attached form a group of the formula

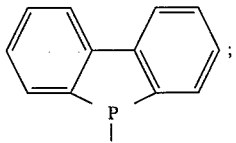

wherein not all of $R^2$, $R^3$, $R^4$ and $R^5$ are the same substituent.

DETAILED DESCRIPTION OF THE INVENTION

The present invention is concerned with novel optically active phosphorus compounds, which, in addition to the pre-determined axial chirality of the biphenyl skeleton, also have centres of chirality at one or both phosphorus atoms, of the formula:

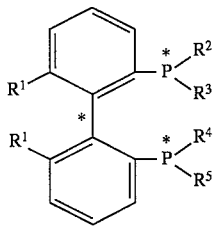     I wherein
$R^1$ is hydroxy, a protected hydroxy group, lower alkyl or lower alkoxy and
$R^2$ to $R^5$ each independently are alkyl with 3 to 7 carbon atoms, cycloalkyl or aryl, or $R^2$ and $R^3$ or $R^4$ and $R^5$ together with the phosphorus to which they are attached form a group of the formula

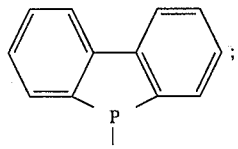

wherein not all of $R^2$, $R^3$, $R^4$ and $R^5$ are the same substituent.

When $R^2$ and $R^3$ together (or $R^4$ and $R^5$ together) are a group of the formula

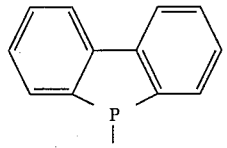

then $R^2$ and $R^3$ (or $R^4$ and $R^5$) are considered to be the same substituent.

Preferred compounds of formula I are compounds in which $R^2$ and $R^4$ are the same substituent, and $R^3$ and $R^5$ are the same substituent but are different substituents from $R^2$ and $R^4$, resulting in compounds of the formula:

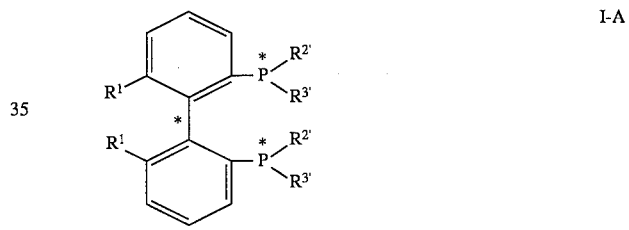     I-A wherein $R^1$ is as above and $R^{2'}$ and $R^{3'}$ are different substituents and are selected from the group consisting of alkyl with 3 to 7 carbon atoms, cycloalkyl and aryl.

Especially preferred compounds of formulae I-A are compounds wherein $R^1$ is lower alkyl, particularly methyl, or lower alkoxy, particularly methoxy, $R^{2'}$ is cycloalkyl or aryl, and $R3'$ is isopropyl, isobutyl or tert.butyl.

Also preferred are compounds of formula I in which $R^2$ and $R^3$ are the same substituent, and $R^4$ and $R^5$ are different substituents, resulting in compounds of the formula:

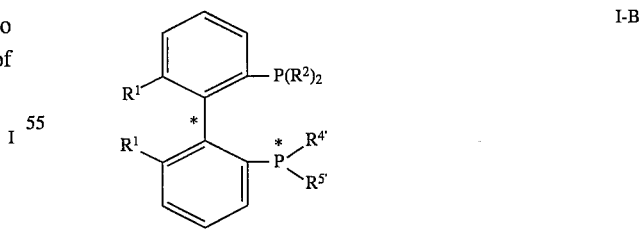     I-B wherein $R^1$ and $R^2$ are as above, and $R^{4'}$ and $R^{5'}$ are different substituents and are selected from the group consisting of alkyl with 3 to 7 carbon atoms, cycloalkyl and aryl.

Especially preferred compounds of formulae I-B are compounds wherein $R^1$ is lower alkyl, particularly methyl, or lower alkoxy, particularly methoxy, $R^2$ and $R^{4'}$ are independently cycloalkyl or aryl, and $R^{5'}$ is isopropyl, isobutyl or tert.butyl.

Particularly preferred compounds are those of formulae I-A and I-B in their optically active form, such as, for example:

(R,S)-, (R,R)- and (S,S)-P-tert.Butyl-P-phenyl-P',P'-diphenyl-(6,6'-dimethylbiphenyl-2,2'-diyl)diphosphine;

(R,S)-, (R,R)- and (S,S)-P-cyclohexyl-P-phenyl-P',P'-diphenyl-(6,6'-dimethylbiphenyl-2,2'-diyl)diphosphine;

(R,S)-, (R,R)- and (S,S)-P-tert.butyl-P-phenyl-P',P'-di-p-tolyl-(6,6'-dimethylbiphenyl-2,2'-diyl)diphosphine;

(R,S,S)-, (S,S,S)- and (R,R,S)-P,P'-di-tert.butyl-P,P'-diphenyl-(6,6'-dimethylbiphenyl-2,2-diyl)diphosphine;

(R,S,S)-, (S,S,S)-and (R,R,S)-P,P'-di-cyclohexyl-P,P'-diphenyl-(6,6'-dimethylbiphenyl-2,2-diyl)diphosphine; and (R,S,S)-, (S,S,S)- and (R,R,S)-P,P'-di-β-naphthyl-P,P'-diphenyl-(6,6'-dimethylbiphenyl-2,2-diyl)diphosphine.

The invention is also concerned with the manufacture of the phosphorus compounds of the invention, their use for enantioselective reactions, such as, e.g., asymmetric hydrogenations, enantioselective hydrogen displacements in prochiral, allylic systems, and the like, as well as complexes of the compounds of formula I with metals of Group VIII. In particular, the compounds of the invention are useful for the preparation of (R)-citronellol (Example 7), a perfume component and intermediate in the production of other perfume components, and (S)-2-acetyl-1-(p-methoxybenzyl)1,2,3,4,5,6,7,8-octahydroisoquinoline (Example 9) and methyl (S)-3-hydroxytetradecanoate (Example 10), which are pharmaceutical intermediates.

The usual ether-forming groups, such as, e.g., benzyl, allyl, benzyloxymethyl, lower alkoxymethyl as well as 2-methoxyethoxymethyl, especially come into consideration in the scope of the present invention as protecting groups for the hydroxy groups.

In the scope of the present application the term "lower alkyl" signifies straight-chain or branched alkyl groups with 1 to 4 carbon atoms, such as, e.g., methyl, ethyl, propyl, isopropyl, n-butyl, isobutyl and tert.butyl. The term "lower alkoxy" signifies groups in which the alkyl residue is as defined above.

The term "alkyl with 3 to 7 carbon atoms" signifies in the present instance straight-chain or branched groups such as, e.g., propyl, isopropyl, n-butyl, isobutyl, tert.butyl, n-pentyl, isopentyl and the like, but especially isopropyl, isobutyl or tert.butyl. In the scope of the present invention "cycloalkyl" stands for 3- to 7membered rings, such as, e.g., cyclopropyl, cyclobutyl, cyclopentyl, cyclohexyl and cycloheptyl, especially for cyclopentyl or cyclohexyl.

The term "aryl" signifies especially the phenyl residue, which can be not only unsubstituted, but also substituted in the ortho-, meta- or para-position or also multiply-substituted. Substituents which come into consideration are, e.g., phenyl, lower alkyl or alkoxy groups, preferably methyl or methoxy groups, or also di-lower alkylamino, preferably dimethylamino or diethylamino, as well as chlorine, or also trialkylsilyl, such as, e.g., trimethylsilyl. Moreover, the term can also signify naphthyl. Preferred aryl residues are especially phenyl, p-tolyl, m-tolyl, m,m'-dimethylphenyl, m,m'-diisopropylphenyl, p-dimethylaminophenyl, p-methoxyphenyl, m-methoxyphenyl, p-methoxy-m,m'-dimethylphenyl, p-chlorophenyl, and β-naphthyl.

While the stereogenic centres in the majority of ligands are localised either only on the hydrocarbon skeleton or only on the phosphorus atoms, such as, for example, in the case of DIPAMP (ethylene-bis[(S)-(2-methoxyphenyl)-phenylphosphine]), only a few examples of ligands which contain stereocentres at both sites are known. Also, these are primarily used for complex formation with transition metals of Group VIII, especially with ruthenium, rhodium or iridium. Such diphosphine-metal complexes are used, for example, as catalysts in asymmetric hydrogenations and also for enantioselective hydrogen displacements in prochiral, allylic systems.

The present invention now makes available optically active phosphine ligands which have a pre-determined axial chirality and which in addition are distinguished by one or two asymmetric phosphorus atoms. The combination of these symmetry elements, chirality axis and chirality centres, in one ligand is novel. These are the compounds of the invention defined above.

The phosphorus compounds of formula I can exist not only in racemic form, but also in optically active form. The process in accordance with the invention for the manufacture of the compounds of the invention comprises reacting a chiral 6,6'-disubstituted 2,2'-diiodobiphenyl of the formula

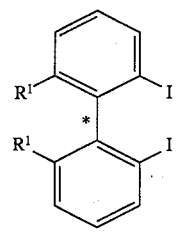

II wherein $R^1$ is as described above, firstly with tert.butyllithium and subsequently with in each case a correpondingly substituted, racemic chlorophosphine derivative of the formula:

$$ClPR^2R^3 \qquad\qquad A$$

and $$ClPR^4R^5 \qquad\qquad B$$

wherein $R^2$ to $R^5$ have the aforementioned significances, in order to obtain the compounds of formula I, or with two chlorophosphine derivatives of formula A in order to obtain the compounds of formula I-A, or reacting a 2-monoiodobiphenyl derivative of the formula

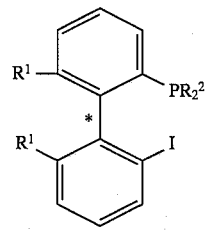

III firstly with tert.butyllithium and subsequently with a correspondingly substituted, racemic chlorophosphine of formula B in order to obtain the compounds of formula I-B.

The compounds of the invention of formulae I-A and I-B are preferably produced in accordance with the following scheme:

Scheme 1

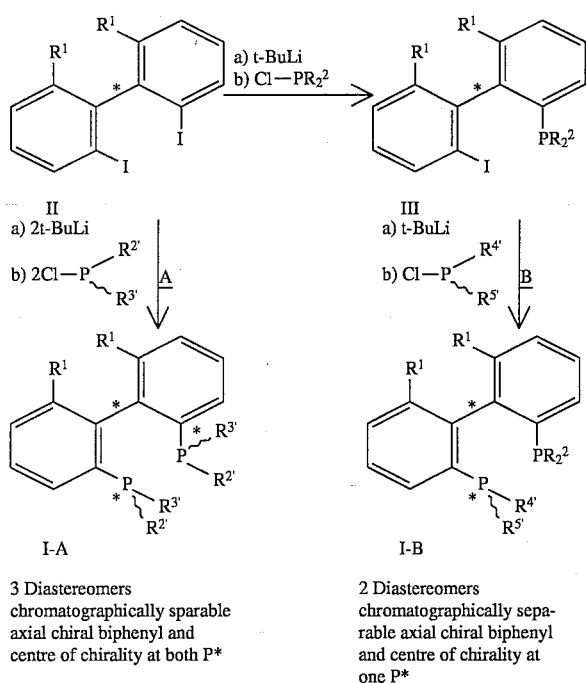

I-A

3 Diastereomers
chromatographically sparable
axial chiral biphenyl and
centre of chirality at both P*

I-B

2 Diastereomers
chromatographically separable axial chiral biphenyl
and centre of chirality at
one P*

The compounds of formula I may also be produced in an analogous manner wherein reactant (b) in the step II→III is ClPR$^2$R$^3$, above.

The advantage of the above reaction procedure is that the chosen configuration of the biphenyl remains unchanged in the reaction. Thereby, a maximum of only three or two diastereomers are possible (I-A or I-B; Scheme 1). In each case, as a result of steric interactions between the asymmetric biphenyl template and the two organic residues on the phosphorus one of the diastereomers is formed in preference directly or after thermal equilibration.

Accordingly, compounds of formula I and I-B can be manufactured in two steps and compounds of formula I-A can be manufactured in a single step starting from compounds of formula II by the process in accordance with the invention.

For the manufacture of the compounds of formula I-A, a diiododiphenyl derivative of formula II is firstly converted with two equivalents of tert.butyllithium in a suitable solvent into the corresponding metallated compound and subsequently reacted with two racemic chlorophosphine derivatives of formula A. The product mixture of three diastereoisomers which is obtained is separated into the individual chiral components by chromatography.

The compounds of formula I-B are manufactured by converting the diiodobiphenyl derivative of formula II used as the starting compound firstly as described above with one equivalent of tert.butyllithium and subsequently with one equivalent of a disubstituted chlorophosphine (ClP(R$^2$)$_2$) into a compound of formula III, which is subsequently reacted with tert.butyllithium and subsequently with one equivalent of a racemic chlorophosphine of formula B. The two diastereomers of formula I-B can be separated by chromatography.

For the manufacture of the compounds of formula I, the diiodide of formula II used as the starting material is firs fly mono-metallated and reacted with one equivalent of the racemic chlorophosphine of formula A and subsequently metallated and then reacted with one equivalent of the racemic chlorophosphine of formula B.

The reaction of the metallated derivatives of compounds II or III with the chlorophosphine is conveniently effected under an inert gas, such as, e.g., argon or nitrogen, in an inert solvent, such as, for example, THF, ether or a mixture of one or both of these with toluene, at temperatures of about −78° to a maximum of −50° C., preferably at about −70° to about −55° C.

The compounds of formulae II and III are known compounds and can be prepared by any conventional means, such as, e.g., as described in WO 93/15090.

The phosphorus compounds of formula I in accordance with the invention form complexes with transition metals of Group VIII, especially with ruthenium, rhodium and iridium, which can be used as catalysts in asymmetric hydrogenations and also for enantioselective hydrogen displacements in prochiral, allylic systems. Ruthenium and rodium complexes are preferred for the mentioned hydrogenations, while rhodium complexes are preferred for isomerizations. These catalysts, i.e., the complexes from a Group VIII metal and the phosphorus compounds of formula I, are novel and are likewise an object of the present invention.

The complexes in question can be manufactured by any conventional means, for example, as described in EP 538 336.

The following Examples illustrate the invention, but are not intended to be a limitation in any manner. In the Examples the selected abbreviations have the following significance:

| | |
|---|---|
| GC | gas chromatography |
| GC-A% | GC-area percent |
| HPLC | high pressure liquid chromatography |
| e.e. | enantiomeric excess |
| d.e. | diastereomeric excess |
| RT | room temperature |

EXAMPLE 1

Manufacture of (R,S)-, (R,R)- and (S,S)-P-tert.butyl-P-phenyl-P',P'-diphenyl-(6,6'-dimethylbiphenyl-2,2'-diyl) diphosphine 14.4 g (0.029 mol) of (S)-diphenyl-(2'-iodo-6,6'-dimethylbiphenyl-2-yl)phosphine were dissolved in a mixture of 200 ml of absolute toluene and 50 ml of ether while gassing with Argon. After cooling to −70° 30 ml of butyllithium solution (1.6M in hexane; 0.048 mol) were added and the reaction mixture was stirred at −69° is for 45 min. Subsequently, 16.0 g (0.080 mol) of (rac)-tert.butyl-phenylchlorophosphine dissolved in 50 ml of toluene were added dropwise at −65° within 15 min. and the grey-beige suspension was stirred at −65° for 1 hr., then at RT overnight.

For the working-up, the mixture was treated with 85 ml of water and 30 ml of 3N NaOH, stirred for 15 min., extracted with 300 ml of toluene. The organic phase was washed twice with 150 ml of water, dried (Na$_2$SO$_4$), filtered and evaporated. After chromatography on 400 g of silica gel (hexane-toluene 1:4–1:1; to toluene) and recrystallization of the two crude fractions [(R,S)-P-tert.butyl-P-phenyl-P',P'-diphenyl-(66'-dimethylbiphenyl -2,2'-diyl)diphosphine: 7.3 g (47% of theory), and (S,S)-P-tert.butyl-P-phenyl-P',P'-diphenyl-(6, 6'-dimethylbiphenyl-2,2'-diyl) diphosphine: 3.9 g (25% of theory)] from AcOEt/MeOH there were obtained.

3.5 g (23% of theory) of (R,S)-P-tert.butyl-P-phenyl-P', P'-diphenyl-(6,6'-dimethylbiphenyl-2,2'-diyl) diposphine, as white crystals, m.p.: 140.9°; (100% e.e., according to HPLC analysis on a Chiracel OD phase; GC content: 99.5%);

$[\alpha]_D^{20}$ +154.3° (c=1; CHCl$_3$), and 2.3 g (15% of theory) of (S,S)-P-tert.butyl-P-phenyl-P',P'-diphenyl-(6,6'-dimethylbiphenyl-2,2'-diyl) diphosphine, as white crystals, m.p.: 142.6°; (100% e.e., according to HPLC analysis on a Chiracel OD phase; GC content: 97%); $[\alpha]_D^{20}$ −121.1° (c=1; CHCl$_3$).

The following compounds were manufactured in an analogous manner using (R)-diphenyl-(2'-iodo-6,6'-dimethylbiphenyl-2-yl)phosphine:

(R,R)-P-tert.Butyl-P-phenyl-P',P'-diphenyl-(6,6'-dimethyl-biphenyl-2,2'-diyl)diphosphine; m.p.: 147°–149°;

(S,R)-)-P-tert.butyl-P-phenyl-P',P'-diphenyl-(6,6'-dimethyl-biphenyl-2,2'-diyl)diphosphine.

EXAMPLE 2

The following compound was manufactured in an analogous manner as in Example 1 using (R)-diphenyl-(2'-iodo-6,6'-dimethylbiphenyl-2-yl)phosphine, but from (rac)-cyclohexylphenylchlorophosphine in place of (rac)-tert.butylphenylchlorophosphine:

(R,R)-P-Cyclohexyl-P-phenyl-P',P'-diphenyl-(6,6'-dimethyl-biphenyl-2,2'-diyl)diphosphine; m.p.: 187.3°–188.1°.

EXAMPLE 3

The following compounds were manufactured in an analogous manner to Example 1 using (S)-di-p-tolyl-(2'-iodo-6,6'-dimethylbiphenyl-2-yl)phosphine:

(R,S)-P-tert.Butyl-P-phenyl-P',P'-di-p-tolyl-(6,6'-dimethyl-biphenyl-2,2'-diyl)diphosphine; m.p.: 161.5°–162°; $[\alpha]_D^{20}$+168.6° (c=0.8; CHCl$_3$), and (S,S)-P-tert.butyl-P-phenyl-P',P'-di-p-tolyl-(6,6'-dimethyl-biphenyl-2,2'-diyl)diphosphine.

EXAMPLE 4

The (S)-diphenyl-(2'-iodo-6,6'-dimethyl-1,1'-biphenyl-2-yl)phosphine used as the starting material in Examples 1 and 2 was prepared as follows:

18 ml of a tert.butyllithium solution (15% solution in pentane; 0.028 mol) were added to a solution, cooled to −76°, of 12.6 g (0.029 mol) of (S)-2,2'-diiodo-6,6'-dimethyl-1,1'-biphenyl dissolved in 200 ml of absolute toluene and 50 ml of ether while gassing with Ar and the mixture was stirred at −70° for 1 hr. Subsequently, a solution of 13 g (0.062 mol) of chlorodiphenylphosphine in 50 ml of absolute toluene was added dropwise from a dropping funnel within 15 min., the mixture was stirred at about +70° for 1 hr. and, after removing the cooling bath, stirred at RT for 1 hr.

For the working-up, the reaction mixture, a grey-beige suspension, was treated with 70 ml of water, made alkaline with 30 ml of 3N NaOH and extracted with 500 ml of ethyl acetate. The organic phase was washed neutral with 150 ml of water, dried (Na$_2$SO$_4$), evaporated and the resulting residue (26 g; yellow oil) was chromatographed on 300 g of silica gel.

In two main fractions there were eluted firstly with 2.1 l of hexane-toluene 6:4 mixture 3.7 g of unreacted starting material (GC content: 75%), and subsequently with 3.5 l of hexane-toluene (1:1) mixture 9.2 g (75%, of theory) of enantiomer-pure (S)-diphenyl-(2'-iodo-6,6'-dimethyl-1,1'-biphenyl-2-yl)phosphine (HPLC: 99.8% ee), as while crystals, which were used directly in the subsequent step. Crystallization from AcOEt/MeOH gave pure (S)-diphenyl-(2'-iodo-6,6'-dimethyl-1,1'-biphenyl-2-yl)phosphine, m.p.: 167.5°–168.4°; $[\alpha]_D^{20}$+43.5° (c=1; CHCl$_3$).

The following starting materials were prepared in an analogous manner:

(rac)-Diphenyl-(2'-iodo-6,6'-dimethyl-1,1'-biphenyl-2-yl)phosphine;

(R)-diphenyl-(2'-iodo-6,6'-dimethyl-1,1'-biphenyl-2-yl)phosphine;

(S)-di-p-tolyl-(2'-iodo-6,6'-dimethyl-1,1'-biphenyl-2-yl)phosphine;

(S)-di-cyclohexyl-(2'-iodo-6,6'-dimethyl-1,1'-biphenyl-2-yl)phosphine;

(S)-di-benzophosphol(2'-iodo-6,6'-dimethyl-1,1'-biphenyl-2-yl)phosphine;

(S)-diphenyl-(2'-iodo-6,6'-dimethoxy-1,1'-biphenyl-2-yl)phosphine; m.p.: 125.7°;

(rac)-diphenyl-(2'-iodo-6,6'-dimethoxy-1,1'-biphenyl-2-yl)phosphine; m.p.: 194.0°–194.4°.

EXAMPLE 5

The ligands of general formula I-A having two chiral P* atoms were manufactured in an analogous manner to Example 1 using (S) 2,2'-diiodo-6,6'-dimethyl-1,1'-biphenyl and in each case double the mount of butyllithium and the corresponding chlorophosphine:

(R,R,S)-P,P'-Di-tert.Butyl-P,P'-diphenyl-(6,6'-dimethylbiphenyl-2,2'-diyl)diphosphine; m.p.: 138.8°; (99.1% d.e.; GC: 97%); $[\alpha]_D^{20}$ +183.5° (c=0.4; CHCl$_3$).

(R,S,S)-P,P'-Di-tert.Butyl-P,P'-diphenyl-(6,6'-dimethylbiphenyl-2,2'-diyl)diphosphine; m.p.: 120.1° (99% d.e.; GC: 98.1%); $[\alpha]_D^{20}$+34.6° (c=0.8; CHCl$_3$).

(S,S,S)-P,P'-Di-tert.Butyl- P,P'-diphenyl-(6,6'-dimethylbiphenyl-2,2'-diyl)diphosphine; m.p.: 143.3°; (99% d.e.; GC: 99.5%); $[\alpha]_D^{20}$−246.0° (c=1; CHCl$_3$).

(R,R,S)-P,P'-Di-cyclohexyl-P,P'-diphenyl-(6,6'-dimethylbiphenyl-2,2'-diyl)diphosphine; m.p.: 190°; (98% d.e.; GC: 98%); $[\alpha]_D^{20}$+160.7°, (c=0.8; CHCl$_3$).

(S,S,S)-P,P'-Di-cyclohexyl-P,P'-diphenyl-(6,6'-dimethylbiphenyl-2,2'-diyl)diphosphine; m.p.: 159°–190° (98% d.e.; GC: 95%); $[\alpha]_D^{20}$ −56° (c=0.5; CHCl$_3$).

(R,R,S)-P,P'-Di-β-naphthyl-P,P'-diphenyl-(6,6'-dimethylbiphenyl-2,2'-diyl)diphosphine; m.p.: 169°–170°; (85% d.e.; GC: 98%).

EXAMPLE 6

6.4 mg (0.0073 mmol) of tetra-m-trifluoroacetato-bis(1,5-cyclooctadiene)diruthenium(II) and 8.1 mg (0.0146 mmol) of (R,S)-P-cyclohexyl-P-phenyl-P',P'-diphenyl-(6,6'-dimethylbiphenyl-2,2'-diyl) diphosphine were dissolved in 100 ml of methanol while stirring at RT in a 100 ml measuring flask in a glove box (O$_2$ content <1 pm). An orange-red, dear catalyst solution formed within 16 hours.

EXAMPLE 7

A 500 ml autoclave was charged in a glove box (O$_2$ content <1 pm) with 27.0 g (175.0 mmol) of geraniol, 36 ml of methanol and 100 ml of catalyst solution prepared according to Example 6. The hydrogenation was carried out at 20° C., a constant pressure of 60 bar of H$_2$ and while stirring intensively. The conversion was 100% after 22 hours. The pale yellow hydrogenation solution was flushed from the autoclave and evaporated on a rotary evaporator at 60°/17 mbar. The residue was distilled at 65°/0.01 mbar. 26.7 g (99.0%) of (R)-citronellol were obtained as a colourless oil, with an enantiomeric purity of 74.3% e.e.. The determination of the e.e. value was effected by GC analysis of the diastereomeric ester prepared with Trolox™ methyl ether.

EXAMPLE 8

10.3 mg (0.0315 mmol) of bis(h-2-acetato)(h-4-1,5-cyclooctadiene)ruthenium(II) and 17.6 mg (0.0315 mmol) of (R,S)-P-cyclohexyl-P-phenyl-P',P'-diphenyl-(6,6'-dimethylbiphenyl-2,2'-diyl) diphosphine were dissolved in a mixture of 6 ml of diethyl ether and 2 ml of tetrahydrofuran in a 50 ml measuring flask in a glove box ($O_2$ content<1 pm), stirred at 40° for 16 hours and subsequently made up to volume with about 42 ml of methanol. An orange-red, clear catalyst solution formed.

EXAMPLE 9

A 500 ml autoclave was charged in a glove box ($O_2$ content <1 pm) with 15.0 g (50.44 mmol) of (Z)-2-acetyl-1-(p-methoxybenzylidene)-1,2,3,4,5,6,7,8 -octahydroisoquinoline, 160 ml of methanol and 10 ml of the catalyst solution prepared according to Example 8. The hydrogenation was effected at 100° and a constant pressure of 35 bar of $H_2$ while stirring intensively. The conversion was 74.0% after 22 hours. An aliquot of the hydrogenation solution (containing about 2 g of crude product) was evaporated at 40°/17 mbar. The residue (1.95 g) consisted of a mixture of 74 GC-A% (S)-2-acetyl-1-(p-methoxybenzyl)-1,2,3,4,5,6,7,8-octahydroisoquinoline: e.e. 91.2% and 26% unreacted educt.

For the determination of the e.e. value, a homogeneous sample of the residue in a mixture of ethylene glycol and 40 percent aqueous KOH solution was hydrolyzed at 170° for 18 hours. The resulting amine was converted in pyridine/4-dimethylaminopyridine with (–)-camphanoyl chloride into a mixture of the diastereomeric amides, which were analyzed by gas chromatography on a PVMS-54 capillary column.

EXAMPLE 10

A 500 ml ml autoclave was charged in a glove box ($O_2$ content <1 pm) with 23.1 g (90.0 mmol) of methyl 3-oxotetradecanoate, 60 ml of methanol and a solution of 5.4 mg (0.009 mmol) of $Ru_2(COD)_2Cl(mCl)_3(CH_3CN)$ (Lit.: E. Singleton et al., S.—Afr. Tydskr. Chem., 40, 183 (1987) and 10.0 mg (0.018 mmol) of (R,S)-P-cyclohexyl-P-phenyl-P', P'-diphenyl -(6,6'-dimethylbiphenyl-2,2'-diyl)diphosphine in 5 ml of dichloromethane. The hydrogenation was effected at 80° and 35 bar. The conversion was 100% after 22 hours.

The hydrogenation solution was concentrated at 50°/17 mbar and the crystalline residue was dissolved in 250 ml of diethyl ether. The ether solution was filtered over 50 g of silica gel in order to separate the catalyst. After concentration and drying of the filtered ether phase there were obtained 22.9 g of methyl (S)-3-hydroxytetradecanoate as white crystals: e.e. 88.5%. For the e.e. determination, a homogeneous sample was esterified with (S)-6-methoxy-2,5,7,8-tetramethylchromane-2-carboxylic acid and the diastereomers were analyzed by gas chromatography on an OV-240-OH capillary column.

We claim:
1. A compound of the formula:

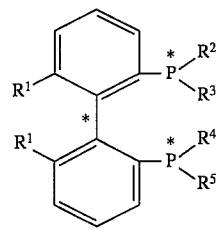

wherein
$R^1$ is hydroxy, a protected hydroxy group, lower alkyl or lower alkoxy; and
$R^2$ to $R^5$ each independently are alkyl with 3 to 7 carbon atoms, cycloalkyl or aryl, or $R^2$ and $R^3$ or $R^4$ and $R^5$ together with the phosphorus to which they are attached form a group of the formula:

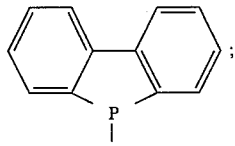

wherein not all of $R^2$, $R^3$, $R^4$ and $R^5$ are the same substituent.

2. The compound of claim 1 having the formula:

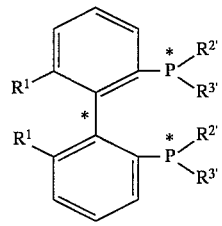

wherein $R^1$ is as in claim 1, and $R^{2'}$ and $R^{3'}$ are different substituents and are selected from the group consisting of alkyl with 3 to 7 carbon atoms, cycloalkyl and aryl.

3. The compound of claim 2 wherein $R^1$ is lower alkyl or lower alkoxy.

4. The compound of claim 3 wherein $R^1$ is methoxy.

5. The compound of claim 4, wherein $R^{2'}$ is cycloalkyl or aryl and $R^{3'}$ is isopropyl, isobutyl or tert.butyl.

6. The compound of claim 3 wherein $R^1$ is methyl.

7. The compound of claim 6, wherein $R^{2'}$ is cycloalkyl or aryl and $R^{3'}$ is isopropyl, isobutyl or tert.butyl.

8. The compound of claim 7 wherein said compound is(R,S)-P-tert.Butyl-P-phenyl-P',P'-diphenyl-(6,6'-dimethylbiphenyl-2,2'-diyl)diphosphine.

9. The compound of claim 7 wherein said compound is(R,R)-P-tert.Butyl-P-phenyl-P',P'-diphenyl-(6,6'-dimethylbiphenyl-2,2'diyl)diphosphine.

10. The compound of claim 7 wherein said compound is(S,S)-P-tert.Butyl-P-phenyl-P',P'-diphenyl-(6,6'-dimethylbiphenyl-2,2-diyl)diphosphine.

11. The compound of claim 7 wherein said compound is(R,S)-Cyclohexyl-P-phenyl-P',P'-diphenyl-(6,6'-dimethylbiphenyl-2,2'-diyl)diphosphine.

12. The compound of claim 7 wherein said compound is(R,R)-P-Cyclohexyl-P-phenyl-P',P'-diphenyl-(6,6'-dimethylbiphenyl-2,2'-diyl)diphosphine.

13. The compound of claim 7 wherein said compound is(S,S)-P-Cyclohexyl-P-phenyl-P',P'-diphenyl-(6,6'-dimethylbiphenyl -2,2'-diyl)diphosphine.

14. The compound of claim 7 wherein said compound is(R,S)-P-tert.Butyl-P-phenyl-P',P'-di-p-tolyl-(6,6'-dimethylbiphenyl -2,2'-diyl)diphosphine.

15. The compound of claim 7 wherein said compound is(R,R)-P-tert.Butyl-P-phenyl-P',P'-di-p-tolyl-(6,6'-dimethylbiphenyl -2,2'-diyl)diphosphine.

16. The compound of claim 7 wherein said compound is(S,S)-P-tert.Butyl-P-phenyl-P',P'-di-p-tolyl-(6,6'-dimethylbiphenyl -2,2'-diyl)diphosphine.

17. The compound of claim 1 having the formula:

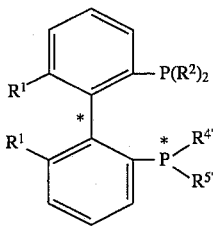

I-B wherein $R^1$ and $R^2$ are as in claim 1, and $R^{4'}$ and $R^{5'}$ are different substituents and are selected from the group consisting of alkyl with 3 to 7 carbon atoms, cycloalkyl and aryl.

18. The compound of claim 17 wherein $R^1$ is lower alkyl or lower alkoxy.

19. The compound of claim 18 wherein $R^1$ is methoxy.

20. The compound of claim 19, wherein $R^2$ and $R^{4'}$ are cycloalkyl or aryl and $R^{5'}$ is isopropyl, isobutyl or tert.butyl.

21. The compound of claim 18 wherein $R^1$ is methyl.

22. The compound of claim 21, wherein $R^2$ and $R^{4'}$ are cycloalkyl or aryl, and $R^{5'}$ is isopropyl, isobutyl or tert.butyl.

23. The compound of claim 22 wherein said compound is (R,S,S)-,P,P'-di-tert.Butyl-P,P'-diphenyl-(6,6'-dimethylbiphenyl-2,2-diyl)diphosphine.

24. The compound of claim 22 wherein said compound is (S,S,S)- P,P'-di-tert.Butyl-P,P'-diphenyl-(6,6'-dimethylbiphenyl-2,2-diyl)diphosphine.

25. The compound of claim 22 wherein said compound is ((R,R,S)-P,P'-di-tert.Butyl-P,P'-diphenyl-(6,6'-dimethylbiphenyl-2,2-diyl)diphosphine.

26. The compound of claim 22 wherein said compound is (R,S,S)-,P,P'-di-Cyclohexyl-P,P'-diphenyl-(6,6'-dimethylbiphenyl-2,2-diyl)diphosphine.

27. The compound of claim 22 wherein said compound is (S,S,S)- P,P'-di-Cyclohexyl-P,P'-diphenyl-(6,6'-dimethylbiphenyl-2,2-diyl)diphosphine.

28. The compound of claim 22 wherein said compound is (R,R,S)-P,P'-di-Cyclohexyl-P,P'-diphenyl-(6,6'-dimethylbiphenyl-2,2-diyl)diphosphine.

29. The compound of claim 22 wherein said compound is (R,S,S)-P,P'-di-β-Naphthyl-P,P'-diphenyl-(6,6'-dimethylbiphenyl-2,2-diyl)diphosphine.

30. The compound of claim 22 wherein said compound is (S,S,S)- P,P'-di-β-Naphthyl-P,P'-diphenyl-(6,6'-dimethylbiphenyl-2,2-diyl)diphosphine.

31. The compound of claim 22 wherein said compound is ((R,R,S)-P,P'-di-β-Naphthyl-P,P'-diphenyl-(6,6'-dimethylbiphenyl-2,2-diyl)diphosphine.

* * * * *